United States Patent [19]

Patel

[11] Patent Number: 5,354,741
[45] Date of Patent: Oct. 11, 1994

[54] DIARYL (PYRIDINIO AND ISOQUINOLINIO) BORON INSECTICIDAL AND ACARICIDAL AGENTS

[75] Inventor: Bomi P. Patel, Philadelphia, Pa.

[73] Assignee: American Cyanamid Company, Wayne, N.J.

[21] Appl. No.: 59,143

[22] Filed: May 7, 1993

[51] Int. Cl.$^5$ ............................................. A01N 55/08
[52] U.S. Cl. ...................................................... 514/64
[58] Field of Search ......................................... 514/64

[56] References Cited

U.S. PATENT DOCUMENTS

| | | | |
|---|---|---|---|
| 3,211,679 | 10/1965 | Updegraff | 260/19 |
| 4,983,589 | 1/1991 | Tszeng | 514/64 |
| 4,983,590 | 1/1991 | Tszeng | 514/64 |

OTHER PUBLICATIONS

H. J. Frohn, et al, Eur. J. Solid State Inorg. Chem., 29(4–5), pp. 729–738 (1992).
W. Regnt, et al, Chem. Ber., 104(3), pp. 722–733 (1971).
J. Soulie and P. Cadiot, Bull. Soc. Chim. France, (6), pp. 1981–1992 (1966).
B. M. Mikhailov and N. S. Fedotov, Zh. Obshch. Khim., 32, pp. 93–95 (1962).
E. W. Abel, et al. J. Chem. Soc., pp. 2895–2897 (1958).
B. M. Mikhailov and N. S. Fedotov, Izvest. Akad. Nauk S.S.S.R., Oldel. Khim. Nauk, pp. 1511–1513 (1956).
R. Koester, et al, Justus Liebigs Ann. Chem., 724, pp. 34–55 (1969).
J. J. Eisch, et al, Heterocycles, 18 (Spec. Issue), pp. 245–250 (1982).

*Primary Examiner*—Allen J. Robinson
*Attorney, Agent, or Firm*—John W. Hogan, Jr.

[57] ABSTRACT

There are provided insecticidal and acaricidal diaryl(-pyridinio and isoquinolinio)boron compounds having the structural formula

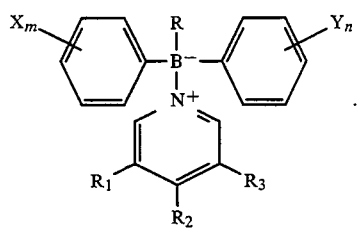

Further provided are compositions and methods comprising those compounds for the protection of plants from attack by insects and acarina.

4 Claims, No Drawings

DIARYL (PYRIDINIO AND ISOQUINOLINIO) BORON INSECTICIDAL AND ACARICIDAL AGENTS

BACKGROUND OF THE INVENTION

Insects and acarina destroy growing and harvested crops. In the United States alone, agronomic crops must compete with thousands of insect and acarid species. In particular, tobacco budworms, southern armyworms and two-spotted spider mites are especially devasting to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids. Also, budworm larvae are difficult to control with currently available insecticides once they reach the third instar.

Two-spotted spider mites attack many plant species, raspberry plants for example, by removing sap from leaves. When raspberry plants are heavily infested, canes and leaves become stunted. With a severe infestation, fruiting canes are damaged, resulting in reduced yield and fruit quality.

In spite of the commercial insecticides and acaricides available today, damage to crops, both growing and harvested, caused by insects and acarina still occurs. Accordingly, there is ongoing research to create new and more effective insecticides and acaricides.

It is therefore an object of the present invention to provide a method for controlling insects and acarina by contacting said insects and acarina, their breeding ground, food supply or habitat with an insecticidally or acaricidally effective amount of a diaryl(pyridinio or isoquinolinio)boron compound.

It is also an object of the present invention to provide a method for protecting growing plants from attack by insects and acarina by applying to the foliage of said plants or to the soil or water in which they are growing an insecticidally or acaricidally effective amount of a diaryl(pyridinio or isoquinolinio)boron compound.

These and other objects of the present invention will become more apparent from the detailed description thereof set forth below.

SUMMARY OF THE INVENTION

The present invention describes insecticidal and acaricidal diaryl(pyridinio and isoquinolinio)boron compounds.

The insecticidal and acaricidal diaryl(pyridinio and isoquinolinio)boron compounds useful in the methods of the present invention have the following structural formula I:

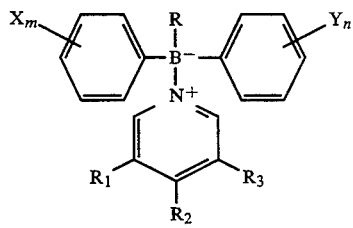

wherein

X and Y are each independently hydrogen, halogen, $C_1$-$C_8$ alkyl, $C_1$-$C_8$ haloalkyl, $C_1$-$C_8$ alkoxy or $C_1$-$C_8$ haloalkoxy;

m and n are each independently an integer of 0, 1, 2 or 3;

R is $C_1$-$C_8$ alkyl, $C_1$-$C_8$ alkoxy, halogen or hydroxy;

$R_1$, $R_2$ and $R_3$ are each independently hydrogen, $C_1$-$C_8$ alkyl, $C_1$-$C_8$ haloalkyl, $C_1$-$C_8$ alkoxy, $C_1$-$C_8$ haloalkoxy, halogen, cyano, nitro, $C(O)R_4$, $NR_5R_6$ or phenyl optionally substituted with one to three halogen, $C_1$-$C_4$ alkyl, $C_1$-$C_4$ haloalkyl, $C_1$-$C_4$ alkoxy, $C_1$-$C_4$ haloalkoxy or $NR_5R_6$ groups, and when taken together, $R_2$ and $R_3$ may form a ring in which $R_2R_3$ is represented by the structure:
—$(CH_2)_p$— or

$R_4$, $R_5$ and $R_6$ are each independently hydrogen or $C_1$-$C_4$ alkyl;

p is an integer of 3 or 4; and

L, M, Q and W are each independently hydrogen, halogen, $C_1$-$C_4$ alkyl, $C_1$-$C_4$ haloalkyl, $C_1$-$C_4$ alkoxy, $C_1$-$C_4$ haloalkoxy or nitro.

This invention also relates to compositions containing those compounds and methods for using those compounds and compositions. Advantageously, it has been found that diaryl(pyridinio and isoquinolinio)boron compounds, and compositions containing them, are effective insecticidal and acaricidal agents for the control of insects and acarina and for the protection of plants from attack by insects and acarina.

DETAILED DESCRIPTION OF THE INVENTION

The present invention provides a method for controlling insects and acarina by contacting said insects and acarina, their breeding ground, food supply or habitat with an insecticidally or acaricidally effective amount of a formula I, diaryl(pyridino or isoquinolinio)boron compound.

The present invention also provides a method for protecting growing plants from attack by insects and acarina by applying to the foliage of said plants or to the soil or water in which they are growing an insecticidally or acaricidally effective amount of a formula I, diaryl(pyridinio or isoquinolinio)boron compound.

The insecticidal and acaricidal diaryl(pyridinio and isoquinolinio)boron compounds of the present invention have the following structural formula I:

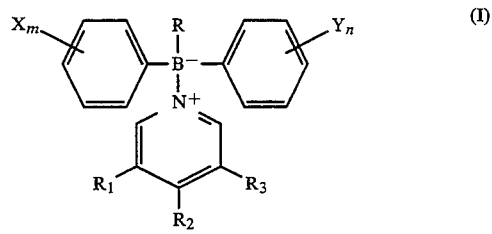

wherein

X and Y are each independently hydrogen, halogen, $C_1$-$C_8$ alkyl, $C_1$-$C_8$ haloalkyl, $C_1$-$C_8$ alkoxy or $C_1$-$C_8$ haloalkoxy;

m and n are each independently an integer of 0, 1, 2 or 3;

R is $C_1$–$C_8$ alkyl, $C_1$–$C_8$ alkoxy, halogen or hydroxy;

$R_1$, $R_2$ and $R_3$ are each independently hydrogen, $C_1$–$C_8$ alkyl, $C_1$–$C_8$ haloalkyl, $C_1$–$C_8$ alkoxy, $C_1$–$C_8$ haloalkoxy, halogen, cyano, nitro, $C(O)R_4$, $NR_5R_6$ or phenyl optionally substituted with one to three halogen, $C_1$–$C_4$ alkyl, $C_1$–$C_4$ haloalkyl, $C_1$–$C_4$ alkoxy, $C_1$–$C_4$ haloalkoxy or $NR_5R_6$ groups, and when taken together, $R_2$ and $R_3$ may form a ring in which $R_2R_3$ is represented by the structure: —$(CH_2)_p$— or

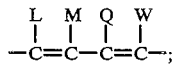

$R_4$, $R_5$ and $R_6$ are each independently hydrogen or $C_1$–$C_4$ alkyl;

p is an integer of 3 or 4; and

L, M, Q and W are each independently hydrogen, halogen, $C_1$–$C_4$ alkyl, $C_1$–$C_4$ haloalkyl, $C_1$–$C_4$ alkoxy, $C_1$–$C_4$ haloalkoxy or nitro.

Preferred formula I insecticidal and acaricidal agents of the present invention are those wherein X and Y are each independently hydrogen, halogen, $C_1$–$C_8$ alkyl or $C_1$–$C_8$ haloalkyl;

m and n are each independently an integer of 0, 1 or 2;

R is $C_1$–$C_8$ alkyl, $C_1$–$C_8$ alkoxy, halogen or hydroxy;

$R_1$, $R_2$ and $R_3$ are each independently hydrogen, $C_1$–$C_8$ alkyl, $C_1$–$C_8$ haloalkyl, halogen, cyano, $C(O)R_4$ or phenyl, and when taken together, $R_2$ and $R_3$ may form a ring in which $R_2R_3$ is represented by the structure: —$(CH_2)_4$— or

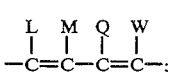

$R_4$ is $C_1$–$C_4$ alkyl; and

L, M, Q and W are each independently hydrogen, halogen, $C_1$–$C_4$ alkyl, $C_1$–$C_4$ haloalkyl or nitro.

More preferred formula I compounds of this invention which are especially effective insecticidal and acaricidal agents are those wherein X and Y are each independently hydrogen, halogen or $C_1$–$C_8$ alkyl;

m and n are each independently an integer of 0, 1 or 2;

R is $C_1$–$C_8$ alkyl;

$R_1$, $R_2$ and $R_3$ are each independently hydrogen, $C_1$–$C_8$ alkyl, halogen, cyano, $C(O)R_4$ or phenyl, and when taken together, $R_2$ and $R_3$ may form a ring in which $R_2R_3$ is represented by the structure : —$(CH_2)_4$— or —CL=CH—CH=CH—;

$R_4$ is $C_1$–$C_4$ alkyl; and

L is hydrogen or nitro.

Still more preferred formula I compounds are those wherein

X and Y are each independently hydrogen, halogen or $C_1$–$C_4$ alkyl;

m and n are each independently an integer of 0, 1 or 2;

R is $C_1$–$C_4$ alkyl; and $R_1$, $R_2$, and $R_3$ are each independently hydrogen, $C_1$–$C_4$ alkyl, halogen, or phenyl, and when taken together $R_2$ and $R_3$ may form a ring in which $R_2 R_3$ is represented by the structure: —CH=CH—CH=CH—.

The term halogen used herein includes fluorine, chlorine, bromine and iodine.

Advantageously, it has been found that the formula I compounds of the present invention are especially useful for the control of tobacco budworms, southern armyworms and two-spotted spider mites.

Insecticidal and acaricidal diaryl(pyridinio and isoquinolinio)boron compounds of formula I wherein R is $C_1$–$C_8$ alkyl may be prepared by reacting a diarylborinic acid ethanolamine ester of formula II with an alkyl magnesium halide of formula III to form an intermediate of formula IV and reacting said formula IV intermediate with a pyridine or isoquinoline of formula V as shown in Flow Diagram I.

FLOW DIAGRAM I

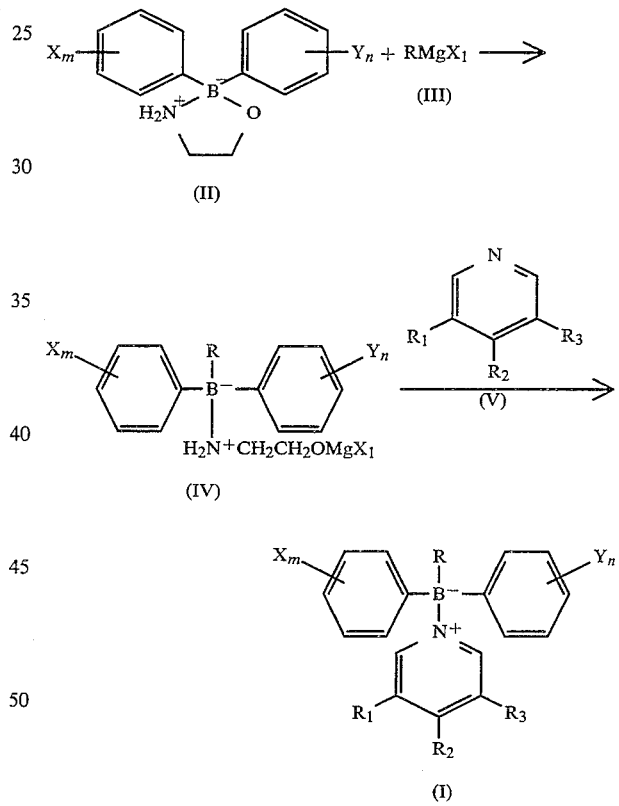

wherein

X, Y, m, n, $R_1$, $R_2$ and $R_3$ are as described hereinabove for formula I;

R is $C_1$–$C_8$ alkyl; and $X_1$ is chlorine, bromine or iodine.

Insecticidal and acaricidal diaryl(pyridinio and isoquinolinio)boron compounds of formula I wherein R is $C_1$–$C_8$ alkoxy, halogen or hydroxy may be prepared by reacting a diarylboron compound of formula VI with a pyridine or isoquinoline of formula V as shown in Flow Diagram II.

FLOW DIAGRAM II

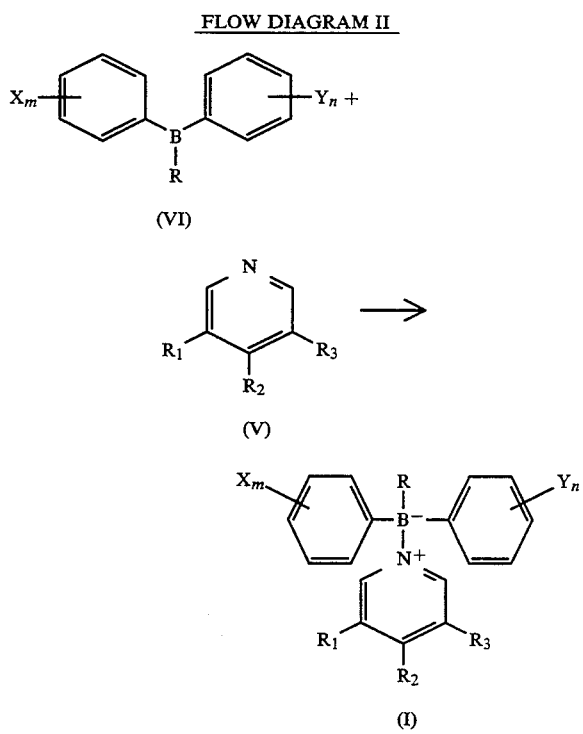

wherein

X, Y, m, n, R$_1$, R$_2$ and R$_3$ are as described hereinabove for formula I; and R is C$_1$–C$_8$ alkoxy, halogen or hydroxy.

The formula I diaryl(pyridinio and isoquinolinio)boron compounds are effective for controlling insects and acarina. Those compounds are also effective for protecting growing or harvested crops from attack by insects and acarina.

Advantageously, it has been found that the formula I compounds of the present invention are especially effective against tobacco budworms, southern armyworms and two-spotted spider mites.

In practice generally about 10 ppm to about 10,000 ppm and preferably about 100 ppm to about 5,000 ppm of a formula I diaryl(pyridinio or isoquinolinio)boron compound, dispersed in water or another liquid carrier, is effective when applied to the plants, the crops or the soil in which said crops are growing to protect said crops from attack by insects and acarina.

The formula I compounds of this invention are also effective for controlling insects and acarina, when applied to the foliage of plants and/or to the soil or water in which said plants are growing in sufficient amount to provide a rate of from about 0.1 kg/ha to 4.0 kg/ha of active ingredient.

While the formula I compounds of this invention are effective for controlling insects and acarina when employed alone, they may also be used in combination with other biological chemicals, including other insecticides and acaricides. For example, the compounds of this invention may be used effectively in conjunction or combination with arylpyrroles, pyrethroids, phosphates, carbamates, cyclodienes, endotoxin of bacillus thuringiensis (Bt), formamidines, phenol tin compounds, chlorinated hydrocarbons, benzoylphenyl ureas and the like.

The formula I compounds of this invention may be formulated as emulsifiable concentrates, flowable concentrates, or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with an inert solid or liquid carrier.

For example, wettable powders, dusts, and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, about 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol or the like.

A typical emulsifiable concentrate can be prepared by dissolving about 15% to about 70% by weight of a diaryl(pyridinio or isoquinolinio)boron compound in about 85% to about 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

In order to facilitate a further understanding of the invention, the following examples are presented to illustrate more specific details thereof. The invention is not to be limited thereby except as defined in the claims.

EXAMPLE 1

Preparation of (5,6,7,8-Tetrahydroisoquinolinio)methyldiphenylboron

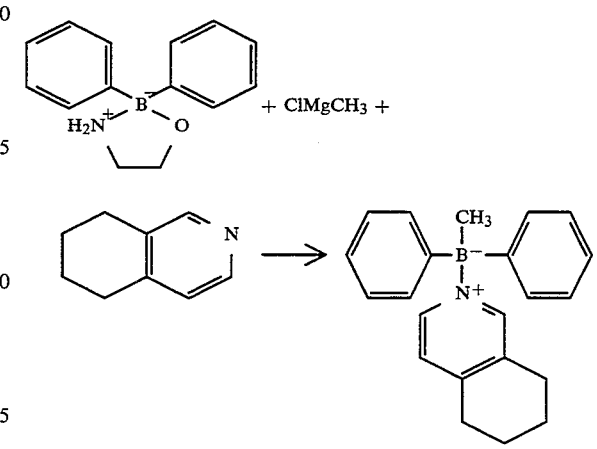

A solution of methyl magnesium chloride in methylene chloride (5.11 mL of a 3 molar solution) is added dropwise to a solution of diphenylborinic acid ethanolamine ester (1.15 g, 5.11 mmol) in tetrahydrofuran. The reaction mixture is stirred for three hours at room temperature, treated with 5,6,7,8-tetrahydroisoquinoline (2.04 g, 15.33 mmol), stirred overnight at room temperature, treated with 5% hydrochloric acid and diluted with ether. The phases are separated and the organic phase is washed sequentially with 5% hydrochloric acid and water, dried over Na$_2$SO$_4$ and concentrated in vacuo to obtain the title product as a white solid (1.41 g, mp 120°–121° C.).

Using essentially the same procedure, and employing methyl magnesium chloride or methyl magnesium bromide and the appropriately substituted pyridine or isoquinoline, the following compounds are obtained:

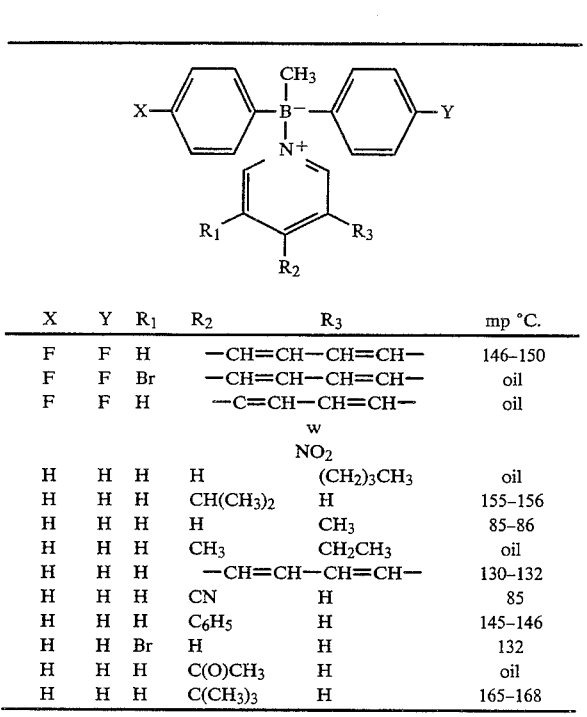

| X | Y | $R_1$ | $R_2$ | $R_3$ | mp °C. |
|---|---|---|---|---|---|
| F | F | H | —CH=CH—CH=CH— | | 146–150 |
| F | F | Br | —CH=CH—CH=CH— | | oil |
| F | F | H | —C=CH—CH=CH— w NO$_2$ | | oil |
| H | H | H | H | (CH$_2$)$_3$CH$_3$ | oil |
| H | H | H | CH(CH$_3$)$_2$ | H | 155–156 |
| H | H | H | H | CH$_3$ | 85–86 |
| H | H | H | CH$_3$ | CH$_2$CH$_3$ | oil |
| H | H | H | —CH=CH—CH=CH— | | 130–132 |
| H | H | H | CN | H | 85 |
| H | H | H | C$_6$H$_5$ | H | 145–146 |
| H | H | Br | H | H | 132 |
| H | H | H | C(O)CH$_3$ | H | oil |
| H | H | H | C(CH$_3$)$_3$ | H | 165–168 |

EXAMPLE 2

Preparation of Chloro(isoquinolinio)di-p-tolylboron

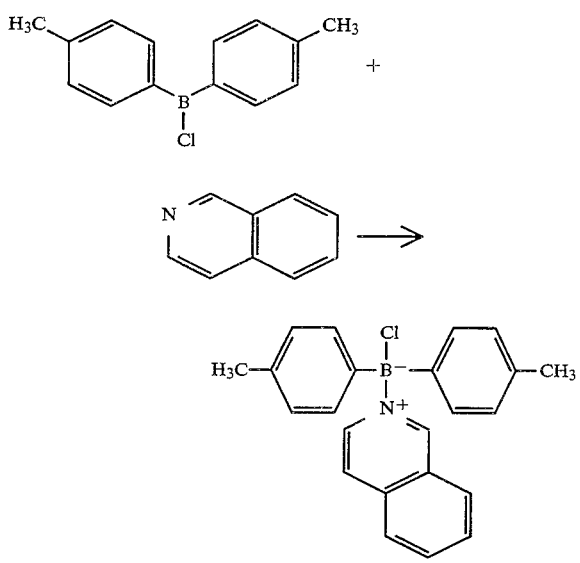

Isoquinoline (0.25 mL, 2.13 mmol) is added to a solution of chloro-di-p-tolylborane (0.5 g, 2.19 mmol) in ether. The reaction mixture is stirred overnight at room temperature and concentrated in vacuo to give the title product as a pale orange oil, 0.7 g, which is identified by $^1$HNMR spectral analysis.

EXAMPLE 3

Preparation of Hydroxy(3-butylpyridinio)diphenylboron

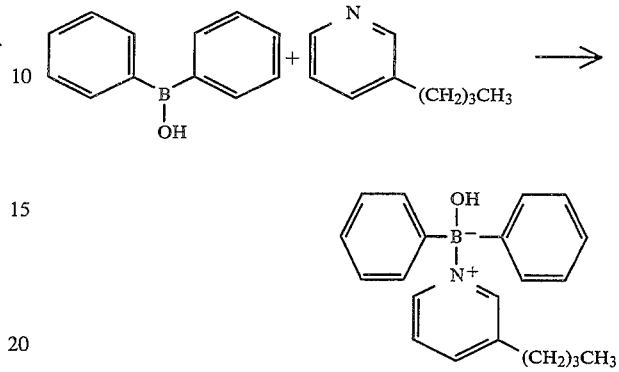

A mixture of diphenylborinic acid (0.5 g, 2.73 mmol) and 3-butylpyridine (0.37 g, 2.74 mmol) in ether is stirred at room temperature for two hours, dried over Na$_2$SO$_4$ and concentrated in vacuo to give the title product as a pale yellow oil, 0.76 g, which is identified by $^1$H and $^{13}$CNMR spectral analyses.

Using essentially the same procedure, but substituting 4-isopropylpyridine for 3-butylpyridine, hydroxy(4-isopropylpyridinio)diphenylboron is obtained as a pale yellow oil.

EXAMPLE 4

Preparation of Butoxy(4-methylpyridinio)diphenylboron

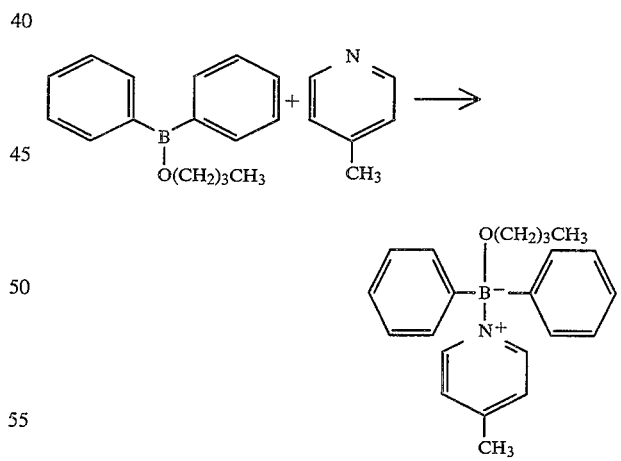

A mixture of butyl diphenylborinate (0.5 g, 2.09 mmol) and 4-picoline (0.206 mL, 2.18 mmol) in ether is stirred for thirty minutes at 0° C. and concentrated in vacuo to obtain the title product as a pale yellow oil, 0.51 g, which is identified by $^1$HNMR spectral analysis.

Using essentially the same procedure, and employing the appropriately substituted pyridine, the following compounds are obtained and characterized by $^1$HNMR spectral analyses:

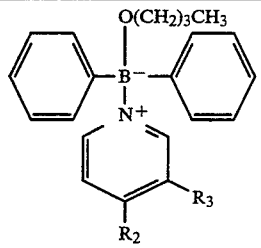

| R₂ | R₃ | |
|---|---|---|
| H | CH₃ | yellow oil |
| CH(CH₃)₂ | H | yellow oil |

EXAMPLE 5

Insecticide and acaricide evaluations

The following tests show the efficacy of the compounds as insecticides and acaricides. The evaluations are conducted with solutions of test compounds dissolved or dispersed in 50/50 acetone/water mixtures. The test compound is technical material dissolved or dispersed in said acetone/water mixtures in sufficient amounts to provide the concentrations set forth in Table I below.

All concentrations reported herein are in terms of active ingredient. All tests are conducted in a laboratory maintained at about 27° C. The rating system employed is as follows:

| RATING SYSTEM | |
|---|---|
| 0 = no effect | 5 = 56-65% kill |
| 1 = 10-25% kill | 6 = 66-75% kill |
| 2 = 26-35% kill | 7 = 76-85% kill |
| 3 = 36-45% kill | 8 = 86-99% kill |
| 4 = 46-55% kill | 9 = 100% kill |
| | - = No evaluation |

The test species of insects and acarina used in the present evaluations along with specific test procedures are described below.

*Spodoptera eridania* 3rd instar larvae, southern armyworm

A sieva lima bean leaf expanded to 7 to 8 cm in length is dipped in the test suspension with agitation for 3 seconds and placed in a hood to dry. The leaf is then placed in a 100×10 mm petri dish containing a damp filter paper on the bottom and 10 3rd instar caterpillars. The dish is maintained for 5 days before observations are made of mortality, reduced feeding or any interference with normal moulting.

*Tetranychus urticae* (OP-resistant strain), 2-spotted spider mite

Sieva lima bean plants with primary leaves expaned to 7 to 8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are dipped in the test formulation for 3 seconds with agitation and set in the hood to dry. Plants are kept for 2 days before estimates of adult kill are made.

*Heliothis virenscens,* 3rd instar tobacco budworm

Cotton cotyledons are dipped in the test formulation and allowed to dry in a hood. When dry, each is cut into quarters and ten sections placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Diabrotica undecimpunctata howardi,* 3rd instar southern corn rootworm

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jars are capped and the contents thoroughly mixed on a Vortex Mixer. Following this, ten 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentration used in this test corresponds to approximately 50 kg/ha.

The data obtained for the above described evaluations are reported in Table I.

TABLE I

| | Insecticide And Acaricide Evaluations | | | | |
|---|---|---|---|---|---|
| | Southern Armyworm (ppm) | | OP. Res. Mites (ppm) | Tobacco Budworm Larvae (ppm) | Southern Corn Rootworm (kg/ha) |
| Compound | 300 | 1000 | 300 | 300 | 50 |
| (4-Isopropylpyridinio)methyldiphenylboron | 8 | — | 8 | 8 | 0 |
| (Isoquinolinio)methyldiphenylboron | 9 | — | 8 | 8 | 9 |
| (3-Ethyl-4-methylpyridinio)methyldiphenylboron | — | 9 | 8 | — | 9 |
| (4-Bromoisoquinolinio)bis(p-fluorophenyl)methylboron | — | 9 | 9 | — | 5 |
| (3-Bromopyridinio)methyldiphenylboron | — | 9 | 7 | — | 0 |
| Methyl(3-methylpyridinio)diphenylboron | — | 9 | 9 | — | 9 |

I claim:

1. A method for controlling insects and acarina which comprises contacting said insects and acarina, their breeding ground, food supply or habitat with an insecticidally or acaricidally effective amount of a compound having the structural formula

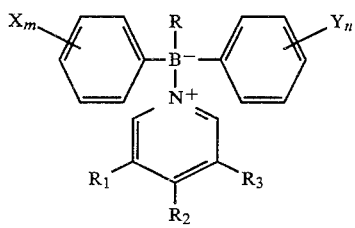

wherein
- X and Y are each independently hydrogen, halogen, $C_1$-$C_8$ alkyl, $C_1$-$C_8$ haloalkyl, $C_1$-$C_8$ alkoxy or $C_1$-$C_8$ haloalkoxy;
- m and n are each independently an integer of 0, 1, 2 or 3;
- R is $C_1$-$C_8$ alkyl, $C_1$-$C_8$ alkoxy, halogen or hydroxy;
- $R_1$, $R_2$ and $R_3$ are each independently hydrogen, $C_1$-$C_8$ alkyl, $C_1$-$C_8$ haloalkyl, $C_1$-$C_8$ alkoxy, $C_1$-$C_8$ haloalkoxy, halogen, cyano, nitro, $C(O)R_4$, $NR_5R_6$ or phenyl optionally substituted with one to three halogen, $C_1$-$C_4$ alkyl, $C_1$-$C_4$ haloalkyl, $C_1$-$C_4$ alkoxy, $C_1$-$C_4$ haloalkoxy or $NR_5R_6$ groups, and when taken together, $R_2$ and $R_3$ may form a ring in which $R_2R_3$ is represented by the structure:
  —$(CH_2)_p$— or

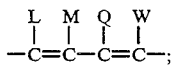

- $R_4$, $R_5$ and $R_6$ are each independently hydrogen or $C_1$-$C_4$ alkyl; p is an integer of 3 or 4; and
- L, M, Q and W are each independently hydrogen, halogen, $C_1$-$C_4$ alkyl, $C_1$-$C_4$ haloalkyl, $C_1$-$C_4$ alkoxy, $C_1$-$C_4$ haloalkoxy or nitro.

2. The method according to claim 1 wherein
- X and Y are each independently hydrogen, halogen, $C_1$-$C_8$ alkyl or $C_1$-$C_8$ haloalkyl;
- m and n are each independently an integer of 0, 1 or 2;
- $R_1$, $R_2$ and $R_3$ are each independently hydrogen, $C_1$-$C_8$ alkyl, $C_1$-$C_8$ haloalkyl, halogen, c phenyl, and when taken together, $R_2$ and $R_3$ may form a ring in which $R_2R_3$ is represented by the structure:
  —$(CH_2)_4$— or

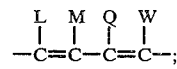

- $R_4$ is $C_1$-$C_4$ alkyl; and
- L, M, Q and W are each independently hydrogen, halogen, $C_1$-$C_4$ alkyl, $C_1$-$C_4$ haloalkyl or nitro.

3. The method according to claim 2 wherein
- X and Y are each independently hydrogen, halogen or $C_1$-$C_8$ alkyl;
- R is $C_1$-$C_8$ alkyl;
- $R_1$, $R_2$ and $R_3$ are each independently hydrogen, $C_1$-$C_8$ alkyl, halogen, cyano, $C(O)R_4$ or phenyl, and when taken together, $R_2$ and $R_3$ may form a ring in which $R_2R_3$ is represented by the structure —$(CH_2)_4$— or —CL=CH—CH=CH—; and
- L is hydrogen or nitro.

4. The method according to claim 3 wherein
- X and Y are each independently hydrogen, halogen or $C_1$-$C_4$ alkyl;
- m and n are each independently an integer of 0, 1 or 2;
- R is $C_1$-$C_4$ alkyl; and
- $R_1$, $R_2$, and $R_3$ are each independently hydrogen, $C_1$-$C_4$ alkyl, halogen, or phenyl, and when taken together $R_2$ and $R_3$ may form a ring in which $R_2R_3$ is represented by the structure: —CH=CH—CH=CH—.

* * * * *